United States Patent [19]

Brown

[11] Patent Number: 4,772,267

[45] Date of Patent: Sep. 20, 1988

[54] PERIPHERAL IV CATHETER WITH ENLARGEABLE FLASHBACK CHAMBER

[75] Inventor: Ronald C. Brown, Santa Cruz, Calif.

[73] Assignee: Menlo Care, Inc., Palo Alto, Calif.

[21] Appl. No.: 31,944

[22] Filed: Mar. 27, 1987

[51] Int. Cl.$^4$ ............................................... A61M 5/32
[52] U.S. Cl. .................................... 604/168; 604/193; 604/263; 604/900
[58] Field of Search ................................ 604/162–169, 604/192, 193, 900, 283, 263, 171, 195; 128/763–770, 767

[56] References Cited

U.S. PATENT DOCUMENTS

| | | | |
|---|---|---|---|
| 3,352,306 | 11/1967 | Hirsch | 604/168 |
| 3,500,828 | 3/1970 | Podhora | 604/168 |
| 3,677,245 | 7/1972 | Welch | 604/193 |
| 3,859,998 | 1/1975 | Thomas et al. | 604/168 |
| 4,710,173 | 12/1987 | McFarlane | 604/168 |

*Primary Examiner*—C. Fred Rosenbaum
*Assistant Examiner*—Colleen Reilly
*Attorney, Agent, or Firm*—Fliesler, Dubb, Meyer & Lovejoy

[57] ABSTRACT

An improvement is set forth in a peripheral IV catheter assembly which comprises a needle hub having proximal and distal ends and a central bore having a flashback chamber, blood in said chamber being observable through said needle hub. A needle extends from the distal end of the bore. A catheter hub fits about the needle and has its proximal end held by the distal end of the needle hub. A cannula fits about the needle with its proximal end engaged with the distal end of the catheter hub. A flashback plug has proximal and distal ends. Its distal end can engage with the proximal end of the needle hub in blocking relation to the needle hub bore. A protector has a proximal end engagable with the distal end of the needle hub with the passage about the catheter hub, the needle and the cannula. The improvement comprises wherein the distal end of the protector is engageable with the proximal end of the needle hub with the central passage in the protector in flow communication with the central bore in the needle hub. The protector is such that blood in the passage is observable through the protector. The flashback plug is adapted intermediate its ends to engage in the passage in the protector. The flashback chamber is extended by connecting it to the central passage in the protector. Also, the flashback plug can be used in the protector to protect against contamination.

3 Claims, 3 Drawing Sheets

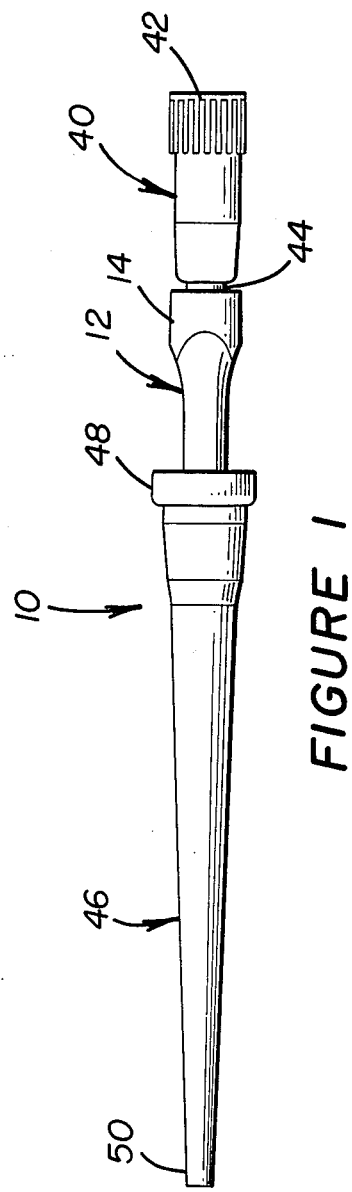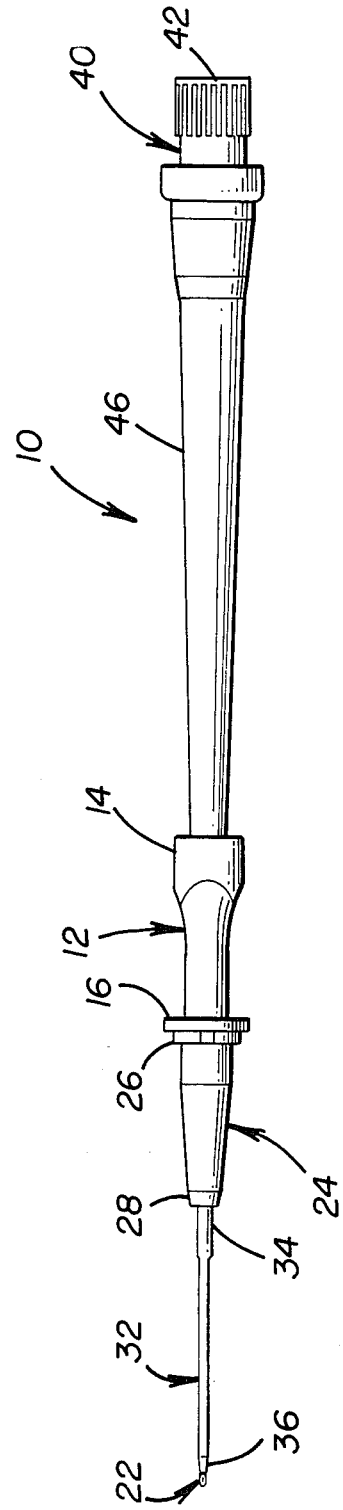

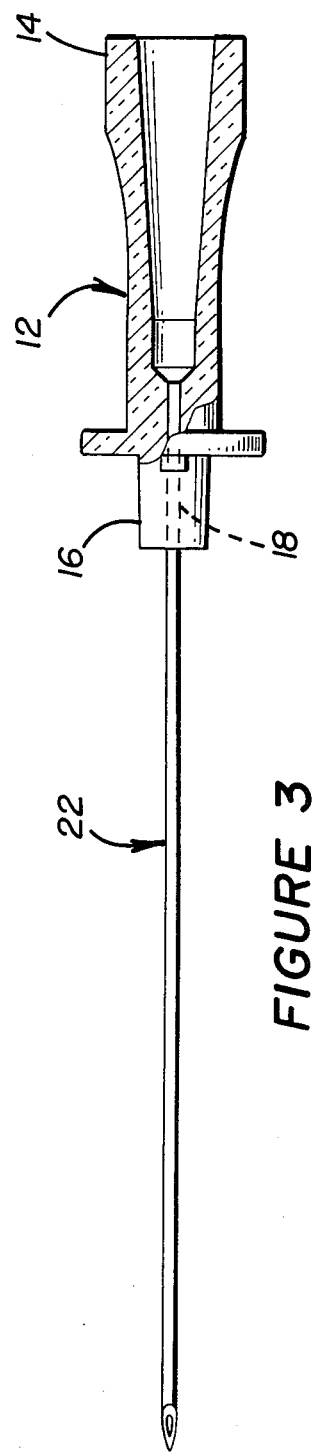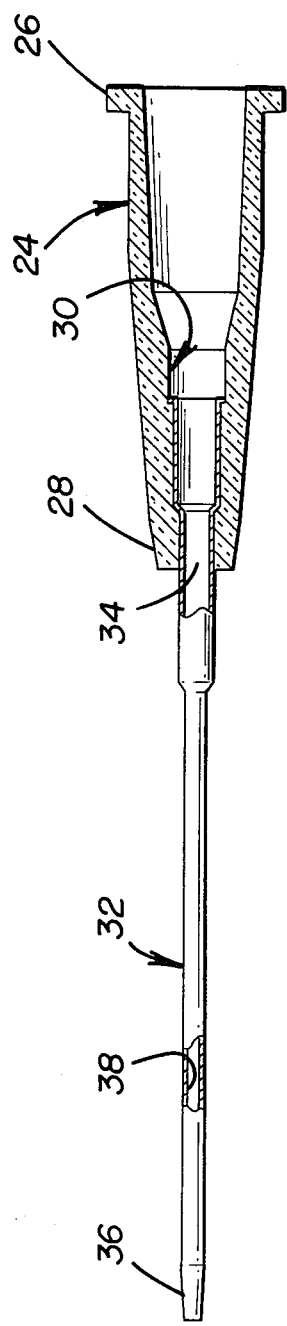

PERIPHERAL IV CATHETER WITH ENLARGEABLE FLASHBACK CHAMBER

TECHNICAL FIELD

The present invention is concerned with peripheral IV catheter assemblies. More specifically, the invention is concerned with an improvement in a peripheral IV catheter assembly which allows the flashback chamber to be significantly extended in length.

BACKGROUND ART

During normal insertion of an IV (intravenous) catheter, positive indication of entry into a vein is shown by blood entering the normally transparent needle hub through the needle. So long as the needle and catheter are in the vein the chamber will continue to fill with blood. If the needle and catheter are pushed in too far, thereby puncturing the distal side of the vein wall and not remaining in the vein lumen, the blood will stop filling the flashback chamber (bore) of the needle hub.

In some medical situations an anesthesiologist will wish to use a 16 gauge or larger catheter. In this case, the large needle size allows blood to fill the flashback chamber so quickly that it is difficult to determine whether the needle is in the vein lumen or has passed through the distal vein wall. Normal practice is to add a syringe to the flashback chamber to provide for extra volume. This is costly and requires the procurement and storing of extra parts. In some cases the syringe plunger is removed making the larger flashback chamber essentially an open reservoir to the air. This can increase the chance of infection.

DISCLOSURE OF INVENTION

The present invention is directed to solving one or more of the problems as set forth above.

In accordance with an embodiment of the present invention an improvement is set forth in a peripheral IV catheter assembly which comprises a longitudinally extending needle hub having a proximal end, a distal end and a central bore defining a flashback chamber, the needle hub being of a construction such that an observer can observe blood in the flashback chamber through the needle hub. A needle is held by the central bore of the needle hub adjacent the distal end of the needle hub and extends longitudinally therefrom. A catheter hub having a proximal end, a distal end and a central bore fits about the needle and has its proximal end held by the distal end of the needle hub. A cannula having a proximal end, a distal end and a central bore fits about the needle with the proximal end of the cannula engaged with the distal end of the catheter hub. A flashback plug having a proximal end and a distal end has its distal end adapted to engage with the proximal end of the needle hub in blocking relation to the bore of the needle hub. A protector has a proximal end, a distal end and a central passage, the proximal end being adapted to engage with the distal end of the needle hub with the passage about the catheter hub, the needle and the cannula. An improvement of the invention comprises a situation wherein the distal end of the protector is adapted to engage with the proximal end of the needle hub with the central passage in flow communication with the central bore of the needle hub; wherein the protector is of a construction such that an observer can observe blood in the passage through the protector; and wherein the flashback plug is adapted to engage the passage adjacent the proximal end of the protector.

The protector is a part which is normally used to protect the catheter and needle from contamination by being touched. Normally protectors are simply thrown away. In accordance with the present invention the dimensions of the narrow end of the protector are made the same as those of the front end of the flashback plug. As a result, the narrow end of the protector can be inserted into the rear of the flashback chamber of the needle hub, with a leak tight fit. This extends the flashback chamber to a size equally that of the needle hub plus that of the protector. The flashback plug also has a second fitment which matches the internal fitment of the large end of the protector. As a result, the flashback plug can be utilized to close off the large end of the protector. No extra parts, such as a syringe, are needed by an anesthesiologist using such a peripheral IV catheter assembly.

BRIEF DESCRIPTION OF THE DRAWINGS

The invention will be better understood by reference to the figures of the drawings wherein like numbers denote like parts throughout and wherein:

FIG. 1 illustrates, in side view, a peripheral IV catheter assembly in accordance with an embodiment of the present invention wherein the protector portion thereof is utilized as a protector;

FIG. 2 illustrates, in side view, the embodiment as in FIG. 1 but wherein the protector is utilized as a flashback chamber extender;

FIG. 3 illustrates, in side section view, the needle hub portion and the needle portion of an embodiment as illustrated in FIGS. 1 and 2;

FIG. 4 illustrates, in side view, partially in section, the catheter hub portion and cannula of an embodiment as illustrated in FIGS. 1 and 2;

BEST MODE FOR CARRYING OUT THE INVENTION

Figure 5:
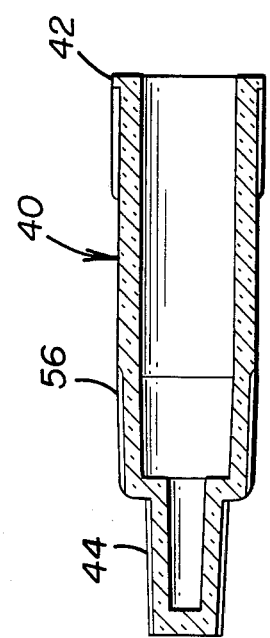
FIG. 5 illustrates, in side sectional view, a flashback plug useful in an embodiment as illustrated in FIGS. 1 and 2.

The present invention is concerned with a peripheral IV catheter assembly 10 illustrated in different modes of use in FIGS. 1 and 2. The peripheral IV catheter assembly 10 comprises a longitudinally extending needle hub 12 having a proximal end 14, a distal end 16 and a central bore 18 which defines a flashback chamber 20. The needle hub 12 is of a construction sufficient so that an observer can observe blood in the flashback chamber 20 through the needle hub 12. This can be accomplished by simply making the needle hub 12 out of a clear or transparent plastic material. Alternatively, a translucent material can be utilized. Also alternatively, the needle hub 12 can be made of an opaque material but an appropriate transparent or translucent sealed window can be present. The needle hub 12 is shown in best detail in FIG. 3. A needle 22 is held by the central bore 18 adjacent the distal end 16 of the needle hub 12. The needle extends longitudinally from the distal end 16 of the needle hub 12.

A catheter hub 24, seen in greatest detail in FIG. 4, has a proximal end 26 and a distal end 28. A central bore 30 extends the length of the catheter hub 24. The catheter hub 24 fits about the needle 22 and has its proximal end 26 held by the distal end 16 of the needle hub 12. Generally a tapered fitment is utilized as shown in FIG. 3 at the distal end 16 of the needle hub 12. The tapered fitment at 16 forms a general mating sealing fit with the central bore 30 of the catheter hub 24 adjacent the proximal end 26 thereof.

A cannula 32, also seen best in FIG. 4, has a proximal end 34, a distal end 36 and a central bore 38. The cannula 32 fits about the needle 22 with the proximal end 34 of the cannula 32 being engaged with the distal end 28 of the catheter hub 24. In the particular embodiment illustrated the proximal end 34 of the cannula 32 fits within the bore 30 of the catheter hub 24 at the distal end 28 thereof.

A flashback plug 40 (see FIGS. 1, 2 and 5) is provided having a proximal end 42 and a distal end 44. The distal end 44 of the flashback plug 40 is adapted to engage with the proximal end 14 of the needle hub 12 in blocking relation to the bore 18 of the needle hub 12. Generally this blocking is accomplished by providing an appropriate tapered fitment at the distal end 44 of the flashback plug 40 which fits against a mating fitment within the bore 18 adjacent the proximal end 14 of the needle hub 12.

Figure 6:
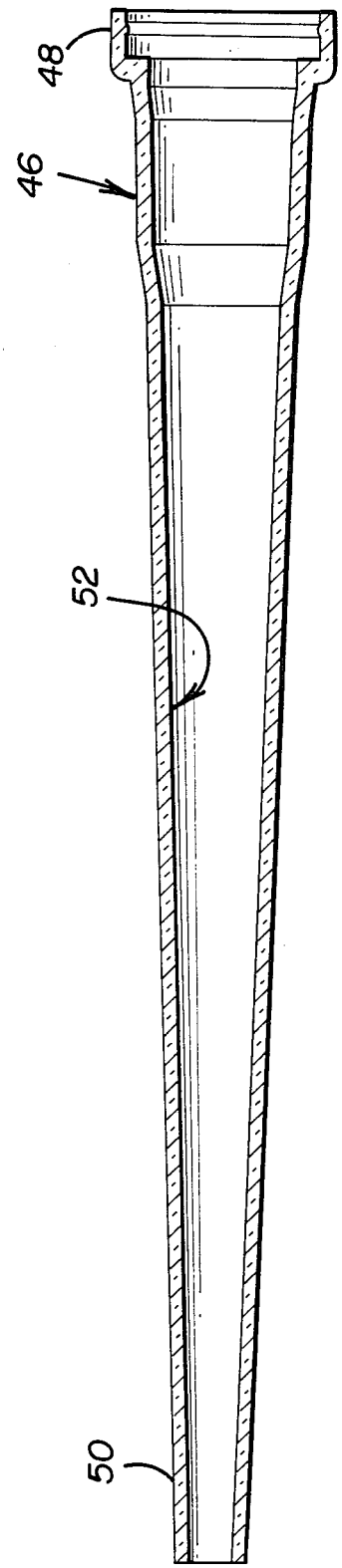
FIG. 6 illustrates, in side sectional view, a protector useful in an embodiment in accordance with FIGS. 1 and 2.

A protector 46 (illustrated most clearly in FIG. 6) has a proximal end 48, a distal end 50 and a central passage 52. The proximal end 48 of the protector 46 is adapted to engage with the distal end 16 of the needle hub 12 with the passage 52 about the catheter hub 24, the needle 22 and the cannula 32.

The configuration in which the peripheral IV catheter assembly 10 would normally be shipped is illustrated in FIG. 1. The protector 46 completely covers both the needle 22 and the cannula 32. In accordance with the present invention certain improvements are set forth which will be described in following and which allow the peripheral IV catheter assembly 10 to be used in the configuration shown in FIG. 2.

In accordance with the present invention the distal end 50 of the protector 46 is adapted to engage with the proximal end 14 of the needle hub 12 with the central passage 52 in the protector 46 in flow communication with the central bore 18 in the needle hub 12. Further, the protector 46 is of a construction such that an observer can observe blood in the passage 52 through the protector 46. For example, it can be transparent, translucent, or have a transparent window, or the like. This allows the protector 46 to be attached so that the passage 52 serve as a continuation of the flashback chamber 20. Since the protector 46 is of a construction such that an observer can observe blood in the passage 50 through the protector 46, the observer can see whether blood is flowing even when using a relatively large gauge needle.

Also in accordance with the present invention the flashback plug 40 is adapted, generally intermediate its proximal end 42 and its distal end 44, to engage in the passage 52 in the protector 46, generally adjacent the proximal end 48 of the protector 46. This provides a capping off of the combination flashback chamber 20 and passageway 52 so as to protect against contamination and/or infection. The flashback plug 40 can be adapted to engage in the passage 52 by, for example, providing a fitment portion 56 thereon, generally of a tapered nature, and generally sufficient to seal against the interior of the passage 52.

INDUSTRIAL APPLICABILITY

The present invention provides a peripheral IV catheter assembly 10 in which the flashback chamber 20 can be extended by the length of the central passageway 52 to aid medical personnel in observing whether the needle 22 is properly placed within the lumen of a vein.

Other aspects, objective and advantages of this invention can be obtained from a study of the drawings, the disclosure and the appended claims.

I claim:

1. In a peripheral IV catheter assembly which comprises a longitudinally extending needle hub having a proximal end, a distal end and a central bore having a flashback chamber, the needle hub being of a construction such that an observer can observe blood in said flashback chamber; a needle held by said central bore of said needle hub adjacent said distal end of said needle hub and extending longitudinally therefrom; a catheter hub having a proximal end, a distal end and a central bore, said catheter hub fitting about said needle and having its proximal end held by said distal end of said needle hub; a cannula having a proximal end, a distal end and a central bore, said cannula fitting about said needle with said proximal end thereof engaged with said distal end of said catheter hub; a flashback plug having a proximal end and a distal end, said distal end of said flashback plug being of a construction such that it engages with said proximal end of said needle hub in blocking relationship with said bore of said needle hub; and a protector having a proximal end, a distal end and a central passage, said proximal end of said protector being of a construction such that it engages with said distal end of said needle hub with said passage about said catheter hub, said needle and said cannula, an improvement comprising:
   whereby said flashback plug is removable from said proximal end of said needle hub;
   wherein said distal end of said protector is of a construction such that it engages with said proximal end of said needle hub with said central passage in said protector in flow communication with said central bore in said needle hub;
   wherein said protector is of a construction such that an observer can observe blood in said passage through said protector;
   wherein said flashback plug is of a construction such that it engages in said passage in said protector; and
   whereby said flashback plug is replaceable in said proximal end of said protector.

2. A peripheral IV catheter assembly as set forth in claim 1, wherein said flashback plug is of a construction such that it engages in said passage in said protector adjacent said proximal end of said protector.

3. A peripheral IV catheter assembly as set forth in claim 1 wherein said flashback plug is of a construction such that it engages in said passage in said protector intermediate said proximal end of said flashback and said distal end of said flashback plug.

* * * * *